US010314698B2

(12) United States Patent
Skemp et al.

(10) Patent No.: US 10,314,698 B2
(45) Date of Patent: Jun. 11, 2019

(54) THERMALLY-ACTIVATED BIOCOMPATIBLE FOAM OCCLUSION DEVICE FOR SELF-EXPANDING HEART VALVES

(71) Applicant: St. Jude Medical, Cardiology Division, Inc., St. Paul, MN (US)

(72) Inventors: Benedict Skemp, Golden Valley, MN (US); Edward E. Parsonage, St. Paul, MN (US); Tracee Eidenschink, Wayzata, MN (US); Aditee Kurane, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 348 days.

(21) Appl. No.: 14/167,423

(22) Filed: Jan. 29, 2014

(65) Prior Publication Data

US 2014/0277428 A1 Sep. 18, 2014

Related U.S. Application Data

(63) Continuation-in-part of application No. 13/797,466, filed on Mar. 12, 2013, now abandoned.

(51) Int. Cl.
*A61F 2/24* (2006.01)
(52) U.S. Cl.
CPC .......... *A61F 2/2418* (2013.01); *A61F 2/2409* (2013.01); *A61F 2/2439* (2013.01); *A61F 2210/0061* (2013.01); *A61F 2230/0065* (2013.01); *A61F 2250/0069* (2013.01)

(58) Field of Classification Search
CPC .................. A61F 2/2409; A61F 2/2427; A61F 2250/0069; A61F 2250/007
See application file for complete search history.

(56) References Cited

U.S. PATENT DOCUMENTS

| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Suba Ganesan
(74) *Attorney, Agent, or Firm* — Lerner, David, Littenberg, Krumholz & Mentlik, LLP (57) ABSTRACT

A structure for sealing a gap between a medical device and adjacent body tissue includes a ring-shaped body formed at least in part of a material that expands from a compressed condition to an expanded condition when heated to a transition temperature and that is adapted to conform to the body tissue in the expanded condition.

11 Claims, 10 Drawing Sheets

(56) References Cited

U.S. PATENT DOCUMENTS

| | | | |
|---|---|---|---|
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 5,980,570 A * | 11/1999 | Simpson | A61F 2/2409 623/2.11 |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,628,804 B2 | 12/2009 | Flagle et al. | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| 8,083,732 B2 * | 12/2011 | Arless | A61B 18/02 606/20 |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,882,786 B2 * | 11/2014 | Bearinger | A61B 17/0057 606/151 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0062788 A1 * | 3/2009 | Long | A61B 18/14 606/41 |
| 2009/0099653 A1 * | 4/2009 | Suri | A61F 2/2418 623/2.11 |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0131058 A1 | 5/2010 | Shadduck | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0137405 A1 * | 6/2011 | Wilson | A61B 17/12022 623/1.19 |
| 2011/0153009 A1 | 6/2011 | Navia et al. | |
| 2011/0166563 A1 * | 7/2011 | Cheng | A61B 18/082 606/30 |
| 2012/0059461 A1 | 3/2012 | Badawi et al. | |
| 2012/0197246 A1 * | 8/2012 | Mauch | A61B 18/1492 606/33 |

(56) References Cited

U.S. PATENT DOCUMENTS

| | | | |
|---|---|---|---|
| 2013/0197622 A1* | 8/2013 | Mitra | A61L 31/145 623/1.15 |
| 2014/0114402 A1* | 4/2014 | Ahlberg | A61F 2/2418 623/2.11 |
| 2014/0222144 A1 | 8/2014 | Eberhardt et al. | |
| 2014/0277428 A1 | 9/2014 | Skemp et al. | |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Quaden et al., "Percutaneous aortic valve replacement: resection before implantation", pp. 836-840, European J. of Cardio-thoracic Surgery, 27 (2005).

Ruiz, Carlos, Overview of PRE-CE Mark Transcatheter Aortic Valve Technologies, Euro PCR, dated May 25, 2010.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

\* cited by examiner

FIG. 1

(PRIOR ART)

THERMALLY-ACTIVATED BIOCOMPATIBLE FOAM OCCLUSION DEVICE FOR SELF-EXPANDING HEART VALVES

CROSS-REFERENCE TO RELATED APPLICATIONS

The present application is a continuation-in-part of U.S. patent application Ser. No. 13/797,466, filed on Mar. 12, 2013, the disclosure of which is incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning collapsible prosthetic heart valves and sealing same in the patient's anatomy to minimize or prevent paravalvular leakage.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's native heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a structure for sealing a gap between a medical device and adjacent body tissue, the structure including a ring-shaped body formed at least in part of a material that expands from a compressed condition to an expanded condition when heated to a transition temperature and that is adapted to conform to the body tissue in the expanded condition.

In some embodiments, a prosthetic heart valve includes a collapsible and expandable stent, a valve assembly disposed in the stent for controlling the flow of blood through the stent and a cuff disposed about the valve assembly, the cuff including a material that expands from a compressed condition to an expanded condition when heated to a transition temperature.

A method of sealing a space between a medical device and adjacent tissue including delivering the medical device and a ring-shaped body to a target site using a delivery system, delivering thermal energy to the ring-shaped body to heat at least a portion of the ring-shaped body to at least a transition temperature, expanding the ring-shaped body from a compressed condition to an expanded condition and sealing the space between the medical device and the adjacent tissue with the expanded ring-shaped body disposed therebetween.

BRIEF DESCRIPTION OF THE DRAWINGS

Various embodiments of the present disclosure are described herein with reference to the drawings, wherein:

FIG. 9 is a diagrammatic view showing another embodiment of a heat-activated ring being activated by forceps; an FIG. 10 is a diagrammatic view showing another embodiment of a heat-activated ring being activated by a balloon.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to the collapsible prosthetic heart valve delivery process, conventional devices suffer from some shortcomings. For example, with conventional self-expanding valves, clinical success of the valve is dependent on accurate deployment and effective sealing within the patient's anatomy. Inaccurate deployment and anchoring may result in the leakage of blood between the implanted heart valve and the native valve annulus, commonly referred to as paravalvular or perivalvular leakage. In aortic valves, this leakage enables blood flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the need to remove a deployed valve. Methods and devices are also desirable that would reduce the likelihood of paravalvular leakage around the implanted heart valve.

There therefore is a need for further improvements to the devices, systems, and methods for transcatheter positioning of collapsible prosthetic heart valves and the sealing of the implanted valves within the patient's anatomy. Specifically, there is a need for further improvements to the devices, systems, and methods for sealing a prosthetic heart valve within a native valve annulus. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user. Also as used herein, the terms "generally," "substantially," and "about" are intended to mean that slight deviations from absolute are included within the scope of the term so modified.

Figure 1:
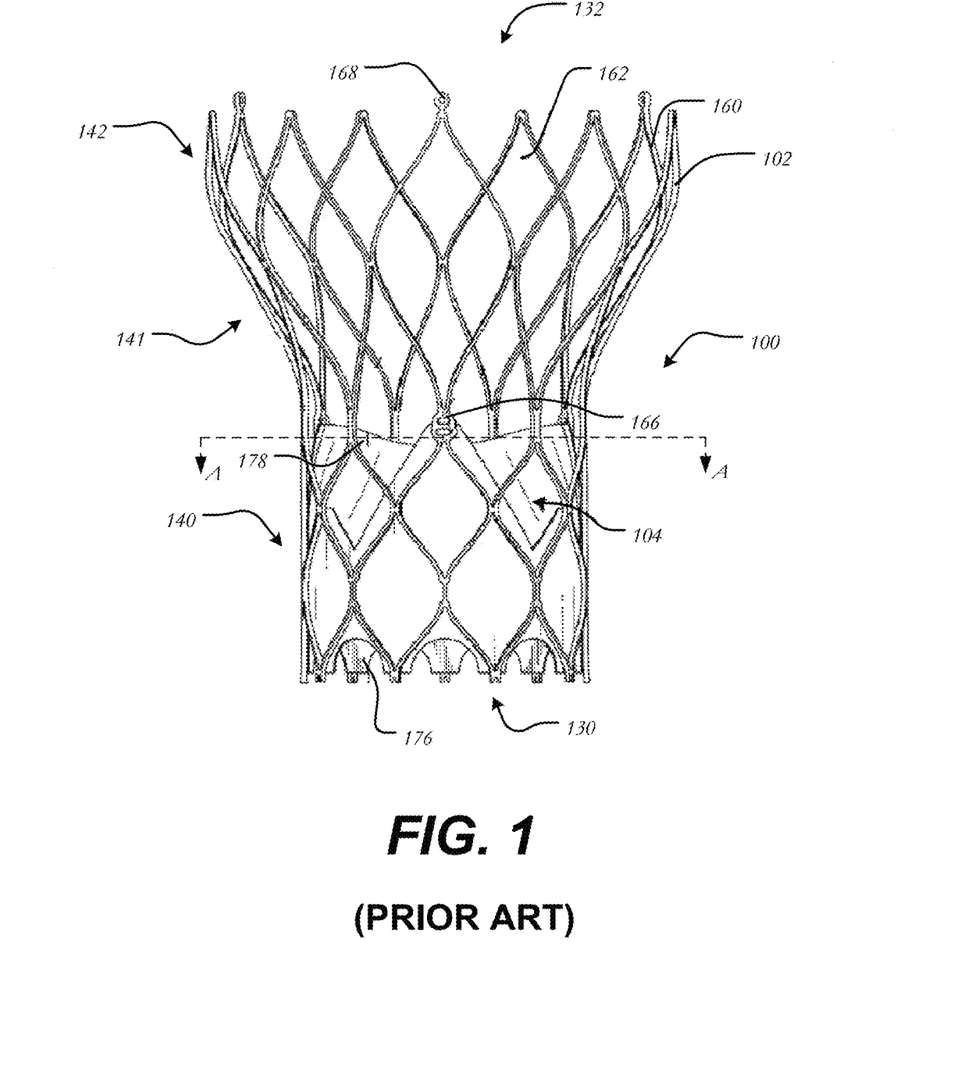
FIG. 1 is a side elevational view of a collapsible prosthetic heart valve.

The biocompatible foams of the present invention may be used in connection with collapsible prosthetic heart valves. FIG. 1 shows one such collapsible stent-supported prosthetic heart valve 100 including a stent 102 and a valve assembly 104 as known in the art. Prosthetic heart valve 100 is designed to replace a native tricuspid valve of a patient, such as a native aortic valve. It should be noted that, while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes an expandable stent 102 which may be formed from, for example, a shape memory material, such as the nickel-titanium alloy known as "Nitinol" or other suitable metals, and in particular, from those materials that are capable of self-expansion. Stent 102 extends from a proximal or annulus end 130 to a distal or aortic end 132, and includes an annulus section 140 adjacent proximal end 130, as well as a transition section 141 and an aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around stent 102. For example, as shown in FIG. 1, annulus section 140 may have two annular rows of complete cells 162 and aortic section 142 and transition section 141 may each have one or more annular rows of partial cells 162. Cells 162 in aortic section 142 may be larger than the cells in annulus section 140. The larger cells in aortic section 142 better enable prosthetic valve 100 to be positioned in the native valve architecture without the stent structure interfering with blood flow to the coronary arteries.

Stent 102 may also include a plurality of commissure features 166 for attaching the commissure between two adjacent leaflets to stent 102. As can be seen in FIG. 1, commissure features 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Valve assembly 104 is secured to stent 102, preferably within annulus section 140 of stent 102. Valve assembly 104 includes cuff 176 and a plurality of leaflets 178 which collectively function as a one-way valve by coapting with one another. As a prosthetic aortic valve, valve 100 has three leaflets 178, as well as three commissure features 166. However, it will be appreciated that other prosthetic heart valves with which the leak occluders of the present invention may be used may have a greater or lesser number of leaflets 178 and commissure features 166.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed from any suitable biological material, such as porcine or bovine pericardial tissue, or from a polymer such as, for example, polytetrafluoroethylene.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly calcified leaflets for proper valve placement and seating could lead to several problems, such as paravalvular leakage (PV leak), which can have adverse clinical outcomes. To reduce these adverse events, the optimal valve would anchor adequately and seal within the native valve annulus without the need for excessive radial force that could harm nearby anatomy and physiology.

Figure 2:
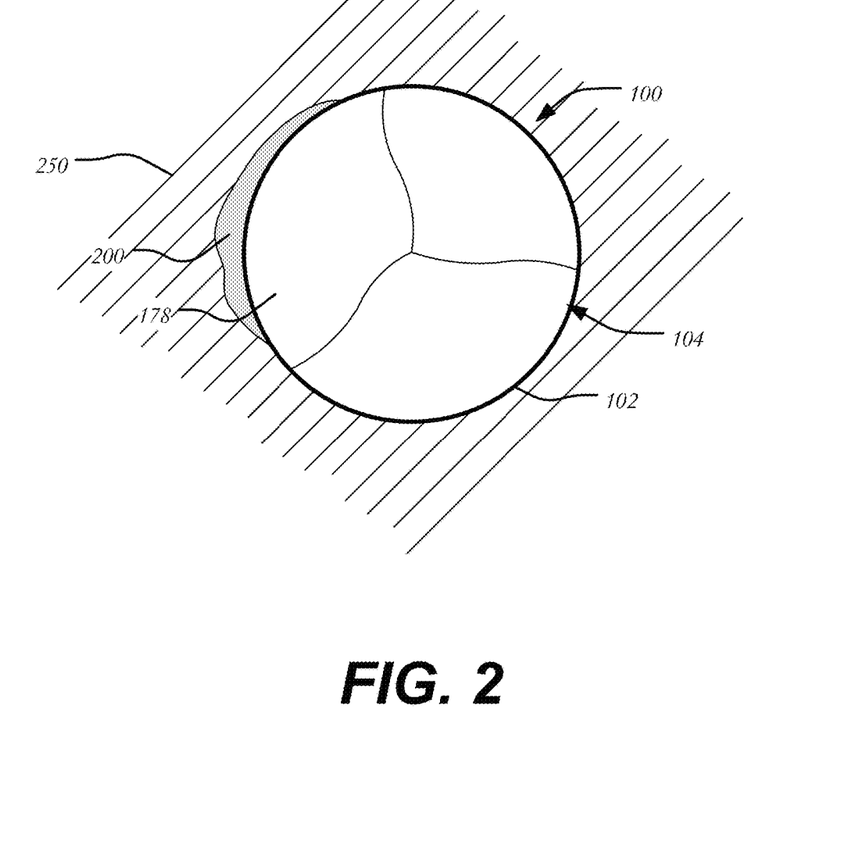
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of stent 102 has a substantially circular cross-section which is disposed within non-circular native valve annulus 250. At certain locations around the perimeter of heart valve 100, crescent-shaped gaps 200 form between the heart valve and native valve annulus 250. Blood flowing through these gaps and around leaflets 178 of valve assembly 104 can cause regurgitation and other inefficiencies which reduce cardiac performance. Such improper fitment may result from sub-optimal native valve annulus geometry due, for example, to calcification of native valve annulus 250 or to unresected native leaflets.

Figure 3A:
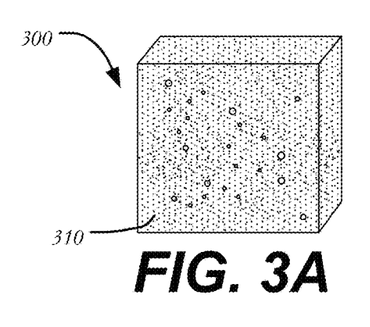
FIG. 3A is a perspective view of an exemplary foam.

FIG. 3A illustrates a biocompatible foam 300 in the shape of body 310. The term "foam" is used herein in an inclusive sense to refer to foamed plastic materials (also sometimes called "cellular plastics", "cellular polymers", "plastic foams" or "expanded plastics"), and more specifically refers to plastic materials in which the apparent density is decreased by the presence of numerous voids disposed throughout its mass. Additionally, body 310 of biocompatible foam 300 may be formed of a polymeric shape-memory material or other suitable material that has the ability to return from a deformed or compressed state to its original or expanded shape. Alternatively, body 310 may be formed of any other compressible foam or material.

Another parameter that may be useful in choosing the proper biocompatible foam 300 is the density of the foam. As previously noted, a foam typically includes voids dispersed throughout its mass, which will decrease the density of the foam. The density of biocompatible foam 300 may be high enough to impede blood flow, but low enough to (1) permit adequate compression such that the foam may be delivered to the target site via a low profile delivery system (e.g., 18 Fr delivery system) and (2) allow the heart valve to fully expand therein. In one example, biocompatible foam 300 may have a density between about 10 kg/m$^3$ and about 200 kg/m$^3$. In other examples, biocompatible foam 300 may have a density between about 45 kg/m$^3$ and about 55 kg/m$^3$.

Biocompatible foam 300 may also be chosen based on the volume change between the compressed state and the expanded state. For example, biocompatible foam 300 may experience a volume change of between about 500% and about 1000% when subjected to its transition temperature or other means of transition. For example, foam 300 may experience a volume change of about 700% when its temperature is raised from 35 degrees Celsius to 37 degrees Celsius.

Figure 3B:
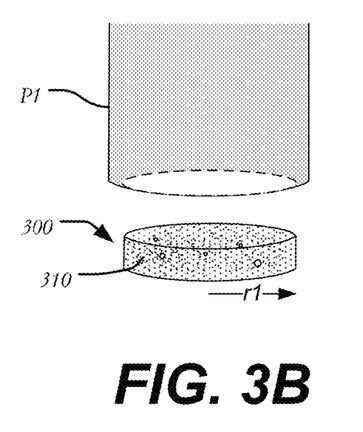
FIG. 3B is a diagrammatic view of the foam of FIG. 3A after it has been die cut into a cylindrical shape.
Figure 3C:
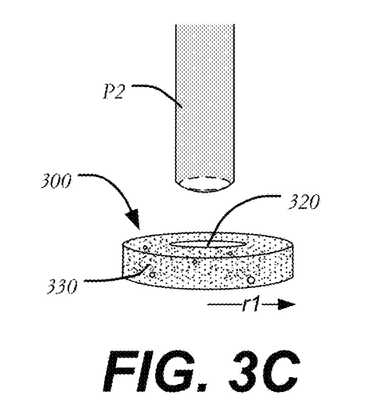
FIG. 3C is a diagrammatic view of the cylindrical foam of FIG. 3B after it has been cut into a ring configuration, the foam ring being in a relaxed configuration.
Figure 3D:
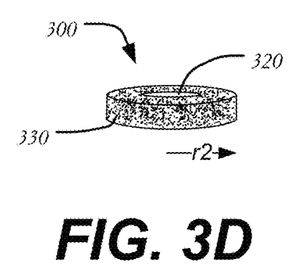
FIG. 3D is a perspective view of the foam ring of FIG. 3C in a deformed condition.

As seen in FIG. 3B, body 310 of biocompatible foam 300 may be cut into a disk having a first radius r1 using a first punch die P1 or any suitable method. Second punch die P2 having a smaller diameter than punch die P1 may be used to remove inner material to form aperture 320 in the disk and thereby create foam ring 330 as shown in FIG. 3C. Ring 330 may have a first radius r1 in its fully-expanded state (FIG. 3C) and a second radius r2 in a deformed or contracted state (FIG. 3D). For example, ring 330 may have a first radius of about 17 mm in its fully-expanded state and may be deformed to a second radius of about 10 mm, which may be further compressed to a radius of about 1.75 mm for delivery and implantation. Moreover, as will be appreciated from FIGS. 3C-3D, aperture 320 may also expand and contract, allowing ring 330 to accommodate an expanding heart valve, as will be shown with reference to FIG. 3E.

The size, shape and density of ring 330 may be adjusted to achieve a desirable profile of radial forces to seal the interstitial space without harming the anatomy. For example, ring 330 may be constructed to have a circumferential stress of about 350 kPa during use. Additionally, as will be appreciated from FIG. 3E, ring 330 will exert a radial force against the supporting stent structure 102 disposed within its aperture 320. In this regard, excess radial force may cause the stent structure to collapse or prevent the stent from fully expanding within the native valve annulus, impeding or reducing the efficiency of the valve assembly. Inadequate radial forces on the other hand may prevent the biocompatible foam of ring 330 from properly sealing the gaps between the walls of the native valve annulus and the heart valve such that paravalvular leakage is not reduced or prevented (i.e., blood will continue to flow around the outside of the heart valve).

One example of initializing shape-memory foam ring 330 for usage includes compressing the size of the ring after cutting it into the proper shape. Specifically, after heating ring 330 above the transition temperature of foam 300 or otherwise coaxing foam 300 to its expanded state (see r1 in FIG. 3C), the ring may be slowly compressed around a mandrel. Once ring 330 has been compressed as desired, it may be removed from the mandrel and quickly blown with compressed air, rapidly dropping the temperature of the ring and locking it into the compressed state. It is to be appreciated that though the compression of ring 330 has been described with reference to heat-activation, other methods of compressing foam 300 may also be used, such as light (e.g., UV light activation) or chemical activation.

Figure 3E:
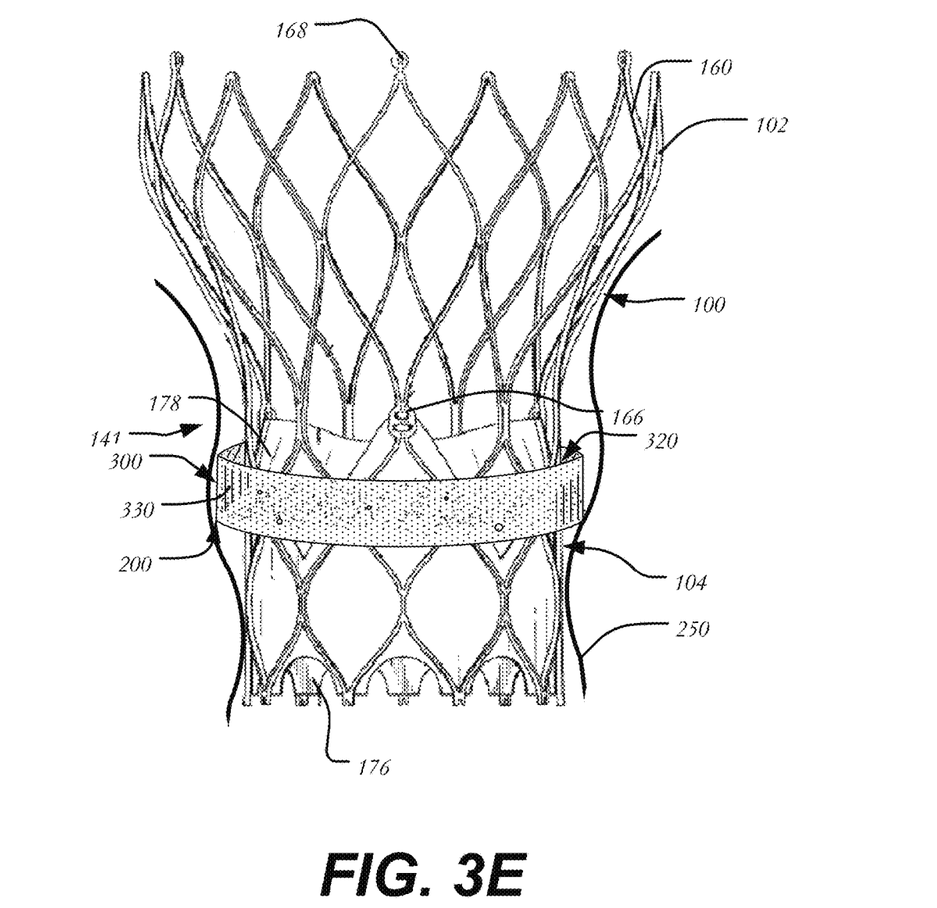
FIG. 3E is a side elevational view of the prosthetic heart valve of FIG. 1 with the foam ring of FIGS. 3C and 3D disposed about the annulus section thereof.

The compressed ring 330 may be placed around the outer circumference of a prosthetic heart valve 100 and attached to heart valve 100 as shown in FIG. 3E. Aperture 320 of ring 330 may be sized so that the ring will be disposed around heart valve 100 near the transition section 141 with a friction fit and no additional attachments. Alternatively, ring 330 may be attached to selected struts 160, cuff 176, commissure features 166 or any other feature or combination of features of prosthetic heart valve 100. Ring 330 may be attached to features of prosthetic heart valve 100 using sutures, a biocompatible glue or adhesive, staples, clips or other suitable methods. Moreover, while FIG. 3E illustrates ring 330 of biocompatible foam 300 disposed about prosthetic heart valve 100 at the position of leaflets 178 in the axial direction, it will be understood that the ring may be arranged at any suitable axial position along stent 102 and that multiple biocompatible foam rings may also be utilized. In at least some examples, at least one of rings 330 overlies a portion of cuff 176. As seen in FIG. 3E, ring 330 forms a foam band about prosthetic heart valve 100 for producing a seal with the native heart tissue. For example, ring 330 may extend about 3 mm to about 5 mm radially outward from the outer circumference of stent 102 when no external force is applied thereupon. As will be described in more detail below, ring 330 allows for superior sealing between the perimeter of heart valve 100 and native valve annulus 250, filling irregularities or gaps 200, while affording a low radial outward force.

FIGS. 4A-D illustrate the steps used to deploy ring 330 to seal prosthetic heart valve 100 within native valve annulus 250. While these figures illustrate transfemoral delivery of a prosthetic valve, it will be understood that ring 330 may be delivered via a transapical, transseptal or any other percutaneous approach. Additionally, ring 330 may be deployed to seal gaps in other locations as well, such as, for example, between the mitral valve and its surrounding tissue.

Figure 4A:
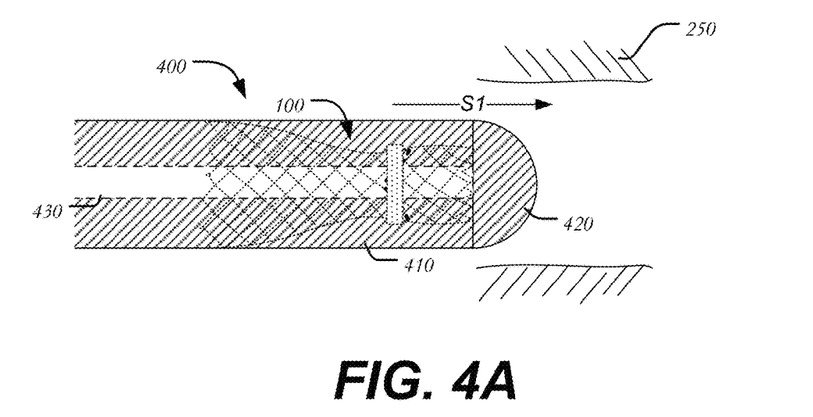
FIGS. 4A-D illustrate the steps used to deploy a prosthetic heart valve having a foam ring within a native valve annulus.

In a first step, heart valve 100, with ring 330 disposed thereabout, may be loaded into a delivery system 400 having an outer sheath 410, an atraumatic tip distal cap 420 and an inner core 430. As shown in FIG. 4A, heart valve 100 may be disposed about core 430 and housed within outer sheath 410. Delivery system 400 may be advanced from the femoral artery, through the common iliac artery to the aorta until reaching native valve annulus 250, as shown by arrow S1 (FIG. 4A). If either heart valve 100 or delivery system 400 includes echogenic materials, such materials may be used to guide the delivery system to the appropriate position using the assistance of three-dimensional echocardiography to visualize the heart valve within the patient.

Figure 4B:
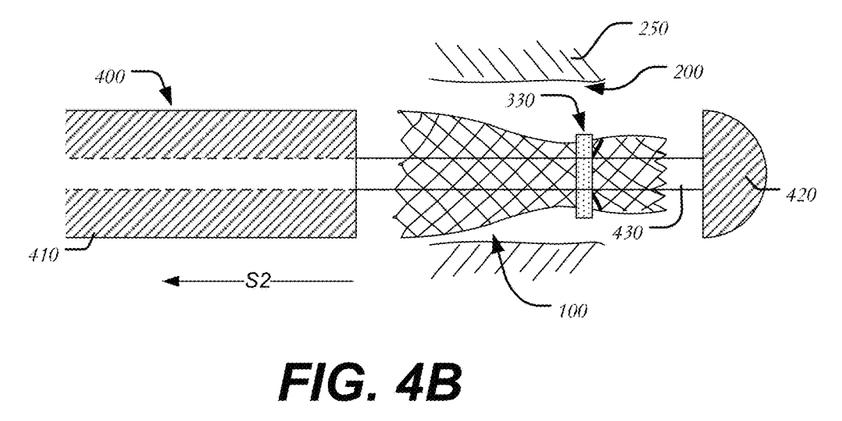
Figure 4C:
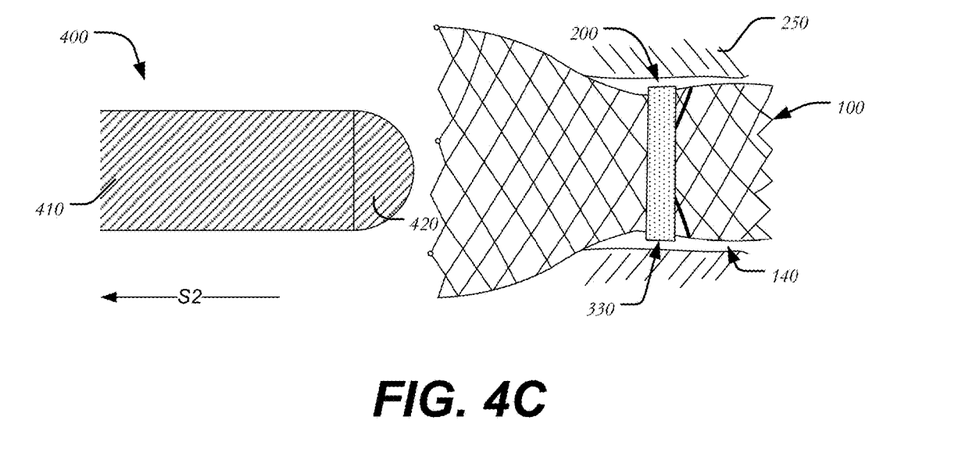

Upon reaching native valve annulus 250, delivery system 400 may be distally advanced until atraumatic tip is positioned at a point beyond the native valve annulus, and outer sheath 410 may be proximally pulled back in the direction of arrow S2 to expose heart valve 100 (FIG. 4B). Self-expanding heart valve 100 may then begin to expand within native valve annulus 250. Foam ring 330 may also begin to expand upon deployment of heart valve 100 (e.g., due to the higher temperature within the patient's body) (FIG. 4C). Alternatively, ring 330 may be flushed with a warm saline solution or other fluids, or otherwise coaxed to promote radial expansion of the foam. Foam ring 330 may also be compressed within sheath 410 and the removal of the sheath may allow the compressed ring to expand to its natural state. Expansion of ring 330 will cause it to fill gaps 200 disposed between heart valve 100 and the walls of native valve annulus 250 and seal the heart valve within native valve annulus 250.

If heart valve 100 fails to perform adequately, for example, due to inadequate coaptation of the leaflets or improper placement, heart valve 100 may be retrieved within sheath 410 and repositioned and/or removed. To this end, various methods may be used to recapture a deployed or partially-deployed valve, such as, for example, through the use of tethers, clips or the like. Once heart valve 100 and foam ring 330 have been properly positioned and fully deployed and expanded, sheath 410 and atraumatic tip 420 may be brought together and delivery system 400 may be proximally pulled through the center of the heart valve in the direction of arrow S2 and removed from the patient's body (FIG. 4C).

Figure 4D:
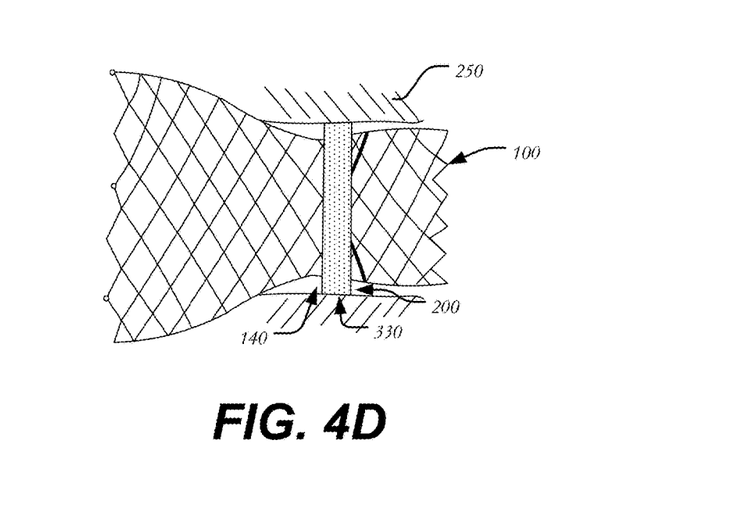

As seen in FIG. 4D, the expanded foam of ring 330 may be compliant and may conform to the surrounding walls of native valve annulus 250. In this figure, heart valve 100 has been implanted in a patient with the annulus portion 140 thereof positioned in native valve annulus 250 and gaps 200 between the heart valve and the native valve annulus have been substantially sealed by foam ring 330.

Figure 5:
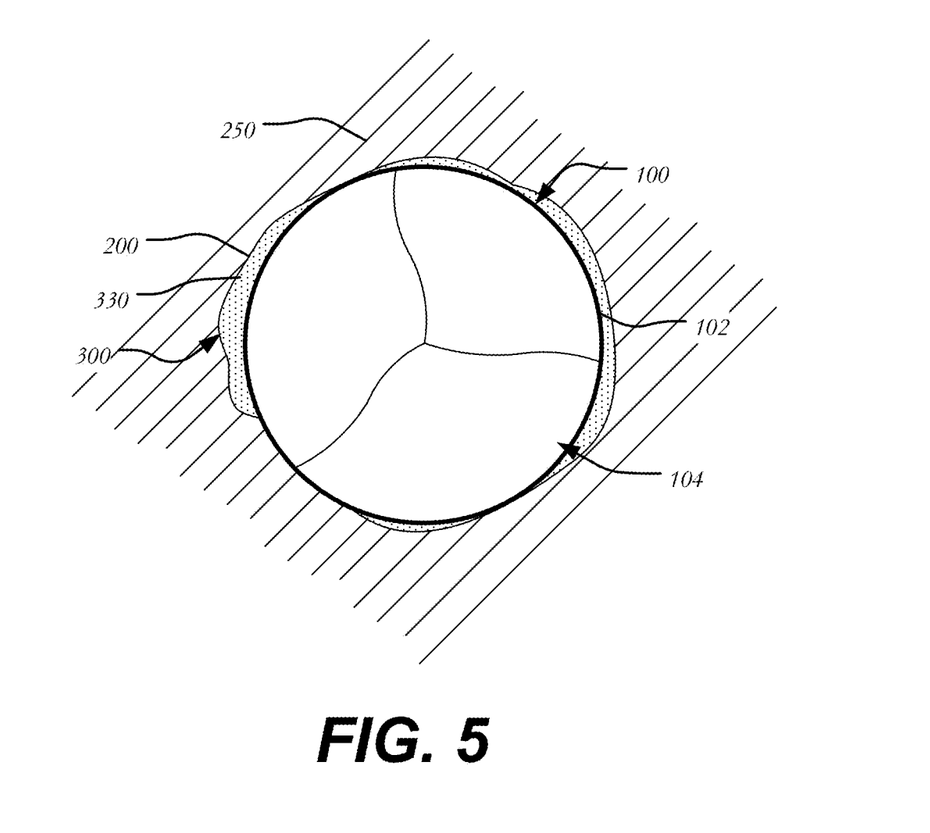
FIG. 5 is a highly schematic cross-sectional view showing a prosthetic heart valve having a foam ring disposed in an expanded state within a native valve annulus.

FIG. 5 is a highly schematic cross-sectional view showing the biocompatible foam of ring 330 in its relaxed state and fully radially expanded to fill crescent-shaped gaps 200 between heart valve 100 and native valve annulus 250. The full thickness of foam 300 may seal larger gaps, while compressed areas of foam 300 will seal smaller gaps and abut against native valve annulus 250. The foam 300 of ring 330 may also be capable of promoting tissue growth between heart valve 100 and native valve annulus 250. For example, foam 300 may be treated with a biological or chemical agent to promote tissue growth on ring 330, further sealing heart valve 100 within native valve annulus 250. Alternatively, foam 300 may be sufficiently dense through the use of polyester fibers or polyester fabric to adequately seal gaps 200 between heart valve 100 and native valve annulus 250 without the need for major tissue growth at gaps 200. When foam 300 is functioning properly, heart valve 100 will be adequately sealed within native valve annulus 250 so that blood flows through valve assembly 104, while limiting or at least reducing blood flow through any gaps formed between the heart valve and the native valve annulus.

Figure 6A:
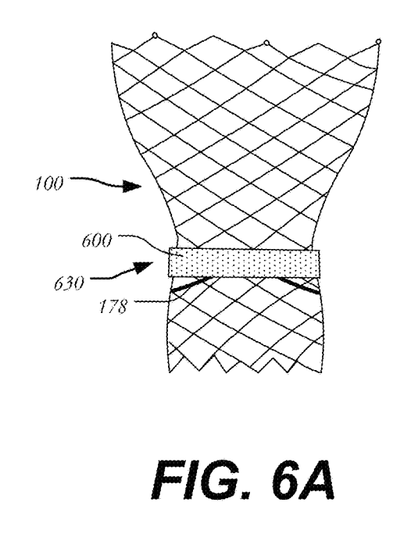
FIGS. 6A-C are diagrammatic views showing a heat-activated ring and the steps used to activate the ring.

FIG. 6A illustrates heart valve 100 having leaflets 178 and material 600, which has been formed into ring 630 disposed about the circumference of heart valve 100 adjacent leaflets 178. Material 600 may be activated using a stimulus, such as a chemical stimulus, light or heat. In some examples, material 600 may be a thermally-activated, shape-memory material including hydrogel compositions and/or foam, which swell or expand upon exposure to an elevated temperature.

In some examples, material 600 may be a heat-activated shape-memory foam capable of changing shape due to a change in temperature such as, for example, by being brought in contact with natural body heat or an external heat source, such as a warm saline injection. The temperature at which material 600 changes from a deformed shape to its original shape or vice versa is referred to as the transition temperature. As used herein, the term "transition temperature" refers to any of a glass transition temperature, a denaturation temperature or a melting temperature of a material.

In one specific example, material 600 may include a biocompatible hydrogel polymer of synthetic (e.g., cross-linked, semi-crystalline high molecular weight polyethylene glycol or polyvinyl alcohol with a melting temperature between about 30 degrees Celsius and about 50 degrees Celsius) or animal-derived origin. Material 600 may instead include an amorphous synthetic polymer such as a polyacrylic acid copolymer having a glass transition at a predetermined transition temperature. In another example, material 600 may include a naturally derived polymer or cross-linked collagen with a denaturation (transition) temperature between about 30 degrees Celsius and about 50 degrees Celsius. Additionally, material 600 may include a thermally-activated shape memory (non-hydrogel) foam having a predetermined density and transition temperature.

Material 600 may have a transition temperature ranging from about 30 degrees Celsius to about 50 degrees Celsius. In some examples, material 600 may have a transition temperature from about 24 degrees Celsius to about 45 degrees Celsius. In some other examples, material 600 may have a transition temperature ranging from about 35 degrees Celsius to about 39 degrees Celsius. Material 600 may have a transition temperature that is within one degree Celsius of normal core body temperature (i.e., about 98.6° F.).

In some examples in which material 600 includes a hydrogel, the hydrogel may have been cross-linked in the swollen state and dried, causing the material to shrink. A thermal transition temperature may be chosen such that room temperature exposure does not result in re-swelling of the hydrogel, but a temperature higher than room temperature results in expansion. As will be shown below, several techniques for heating material 600 past the transition temperature using an activating device are possible.

Figure 6B:
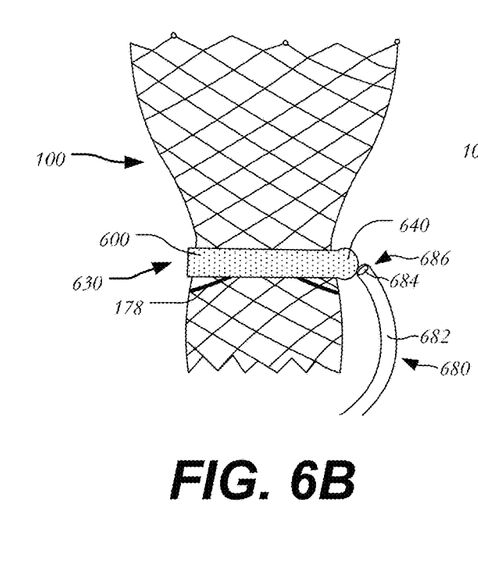
Figure 6C:
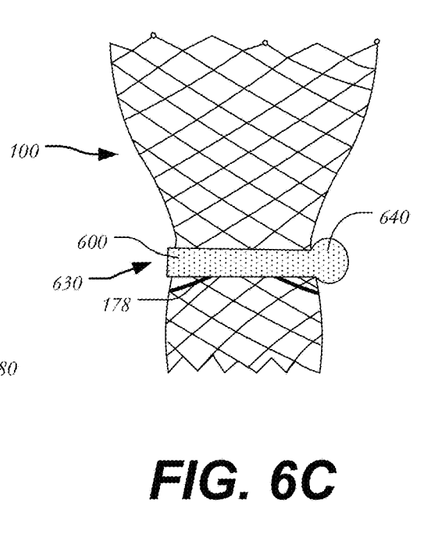

FIG. 6B illustrates the use of ablation catheter 680 to activate material 600. In a simple configuration, ablation catheter 680 may include an elongated shaft 682 terminating in an ablation electrode 684 at terminal end 686 of shaft 682. Ablation electrode 684 may be capable of heating material 600 by delivering radiofrequency energy, such as a high-frequency alternating current. As thermal energy is delivered to material 600, portions of material 600 that are heated begin to expand. FIG. 6B illustrates localized expansion of heated zone 640 of material 600, which has been heated above the transition temperature. As more thermal energy is delivered to material 600, more portions of material 600 form expanded heated zones 640. Once the desired portions of material 600 have sufficiently expanded to provide the desired paravalvular leakage protection between heart valve 100 and the surrounding tissue, ablation catheter 680 may be removed from the patient's body (FIG. 6C).

Figure 7A:
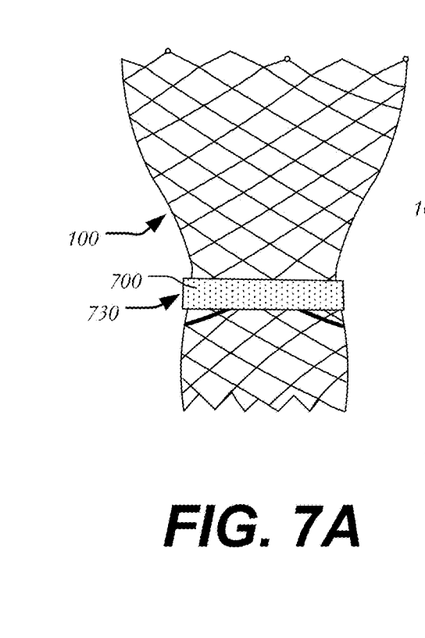
FIGS. 7A-C are diagrammatic views showing another embodiment of a heat-activated ring and the steps used to activate the ring.
Figure 7B:
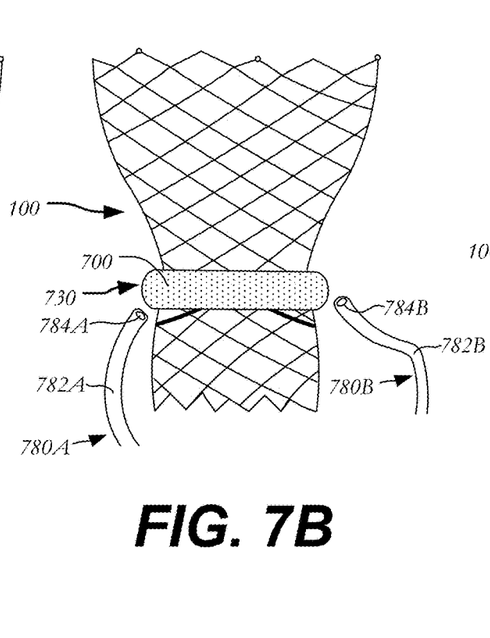
Figure 7C:
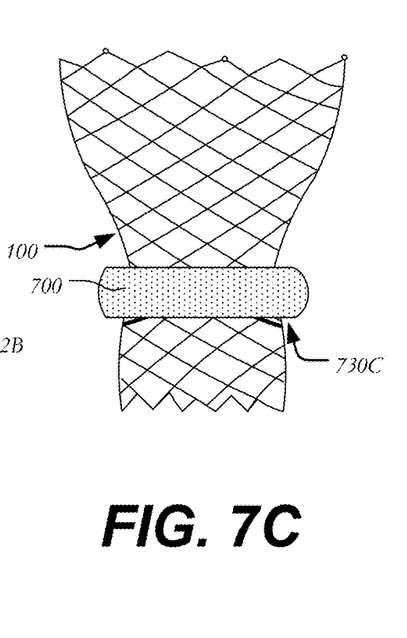

FIGS. 7A-C illustrate another embodiment of a heat-activated material 700 formed into ring 730 disposed about heart valve 100. In this embodiment, instead of expanding only in localized heated zones, material 700 radially expands uniformly. As shown in FIG. 7B, a first ablation catheter 780A having a first shaft 782A and a first ablation electrode 784A heats one portion of ring 730, while a second ablation catheter 780B having a second shaft 782B and a second ablation electrode 784B heats a diametrically opposed portion of ring 730. First and second ablation catheters 780A, 780B may be revolved about ring 730 to heat different regions. Alternatively, a single ablation catheter may be manipulated to uniformly heat ring 730. The resulting ring 730C is uniformly expanded both radially and longitudinally to impede paravalvular leakage (FIG. 7C).

Figure 8:
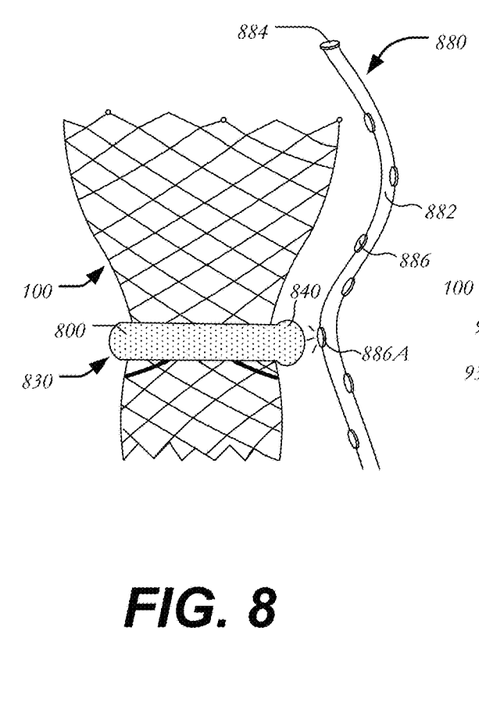
FIG. 8 is a diagrammatic view showing another embodiment of a heat-activated ring being activated by a guidewire.

FIG. 8 illustrates another embodiment of a heat-activated ring being activated by a guidewire. Heart valve 100 has been fitted with material 800 in the form of ring 830. In this embodiment, guidewire 880 includes an elongated shaft 882 having a leading electrode 884 and a plurality of trailing electrodes 886. Guidewire 880 may be introduced into the patient's body and advanced to the site of paravalvular leakage. Guidewire 880 may include at least on localization feature for guiding guidewire 880 to the implant location and positioning electrodes 884, 886 in the desired location relative to ring 830. In one example, electrodes 884, 886 may be radiopaque and techniques such as fluoroscopy may be used to properly align the electrodes with the portion of ring 830 that needs to be expanded. In another example, guidewire 880 may be a MediGuide Enabled™ device such that precise localization and orientation may be determined. Once in position, one or more electrodes 886A may be activated to provide thermal energy to a portion of ring 830, such as heated region 840, to expand the material 800 thereat.

Figures 9, 10:
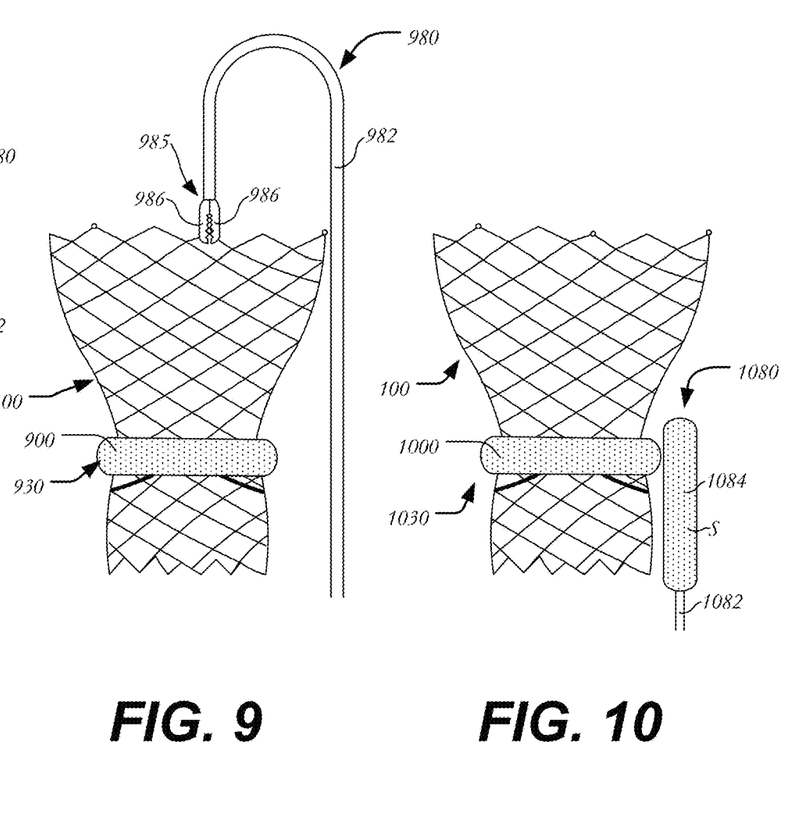

FIG. 9 illustrates another embodiment of a heat-activated ring being activated by forceps. Heart valve 100 having metallic stent 102 has been fitted with material 900 in the form of ring 930. Material 900 is activated using forceps 980, which includes jaws 986 coupled to terminal end 485 of elongated shaft 982. Forceps 980 are configured to grasp and transmit heat to a portion of stent 102. As stent 102 heats, thermal energy is transmitted to material 900, which begins to expand to impede paravalvular leakage. It will be understood that forceps 980 may be disposed either to one side of metallic stent 102 or may extend through stent 102.

FIG. 10 illustrates another embodiment of a heat-activated ring being activated by a balloon. Heart valve 100 has been fitted with material 1000 in the form of ring 1030. In this example, balloon catheter 1080 is used to heat material 1000. Balloon catheter 1080 may generally include hollow shaft 1082 coupled to balloon 1084. Warm saline (e.g., warmer than body temperature) or other medium may be delivered via shaft 1082 to balloon 1084 to transfer heat energy to material 1000 to activate it.

Rather than applying an expandable ring around the exterior of stent 102 of prosthetic heart valve 100, cuff 176 of heart valve 100 may be impregnated with an expandable heat-activated material, such as a heat-activated hydrogel. This heat-activated material may be impregnated through cuff 176 or only in selected regions. Using any of the techniques described above, the heat-activated material may be subject to thermal energy to expand the entire cuff 176 or only selected regions thereof as desired to impede paravalvular leakage. In such examples, preferably, cuff 176 is disposed on the abluminal surface so as to easily expand and seal heart valve 100 against the native valve annulus.

While the inventions herein have been described for use in connection with heart valve stents having a particular shape, the stent could have different shapes, such as a flared or conical annulus section, a less-bulbous aortic section, and the like, and a differently shaped transition section. Additionally, though biocompatible material has been described for use in connection with expandable transcatheter aortic valve replacement, it may also be used in connection with surgical valves, sutureless valves and other devices in which it is desirable to create a seal between the periphery of the device and the adjacent body tissue. Although the deployment of biocompatible material has been described using a catheter that deploys prosthetic heart valve 100 in tandem with a ring, it will be understood that the heart valve may be delivered first, followed by the ring. It will also be understood that while the preceding disclosure has illustrated the use of a single ring to fill gaps, multiple rings and other structures may be deployed at different lateral sections of a heart valve.

Moreover, although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

In some embodiments, a biocompatible structure for sealing a gap between a medical device and adjacent body tissue includes a ring-shaped body formed at least in part of a material that expands from a compressed condition to an expanded condition when heated to a transition temperature and that is adapted to conform to the body tissue in the expanded condition.

In some examples, the transition temperature may be a crystalline melting point of the material; and/or the transition temperature may be a temperature at which the material undergoes a glass transition; and/or the transition temperature may be a denaturation temperature of the material; and/or the material may be a shape-memory material; and/or the shape-memory material may include a hydrogel polymer; and/or the shape-memory material may include an amorphous synthetic polymer; and/or the shape-memory material may include a cross-linked naturally-derived polymer; and/or the medical device may be a prosthetic heart valve having a collapsible and expandable stent, a valve assembly disposed in the stent for controlling the flow of blood through the stent, and a cuff disposed about the valve assembly, and wherein the body overlaps with a portion of the cuff; and/or wherein, in a use condition, the material in only a localized portion of the body may be placed in the expanded condition; and/or wherein, in a use condition, the entire body may be substantially uniformly placed in the expanded condition.

In some embodiments, a prosthetic heart valve includes a collapsible and expandable stent, a valve assembly disposed in the stent for controlling the material in the flow of blood through the stent and a cuff disposed about the valve assembly, the cuff including a material that expands from a compressed condition to an expanded condition when heated to a transition temperature. The material may include a hydrogel.

In some embodiments, a method of sealing a space between a medical device and adjacent tissue includes delivering the medical device and a ring-shaped body to a target site using a delivery system, the body being formed at least in part of a material that expands from a compressed condition to an expanded condition when heated to a transition temperature and delivering thermal energy to the ring-shaped body to heat the material in at least a portion of the body to at least the transition temperature, whereas the material in the portion the body expands to seal the space between the medical device and the adjacent tissue with the expanded body disposed therebetween.

In some examples, the thermal energy may be supplied by an ablation catheter having at least one ablation electrode; and/or the at least one ablation electrode may be configured to deliver high-frequency alternative current to the ring-shaped body; and/or the thermal energy may be supplied by a plurality of ablation catheters; and/or the thermal energy may be supplied by a guidewire having at least one localization feature and at least one electrode for delivering the thermal energy; and/or the at least one localization feature may include a radiopaque electrode; and/or the thermal energy may be supplied by forceps configured to grasp the medical device and transmit heat to the body; and/or the thermal energy may be supplied by a balloon catheter comprising a balloon fillable with a warm medium.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of sealing a space between a prosthetic heart valve and adjacent tissue, the method comprising:
    loading the prosthetic heart valve into a delivery system including compressing a ring-shaped body disposed on an outer surface of the prosthetic heart valve and coupled to the prosthetic heart valve;
    delivering the prosthetic heart valve and the ring-shaped body to a target site using the delivery system;
    deploying the prosthetic heart valve and the ring-shaped body at the target site concurrently, including releasing the ring-shaped body from the delivery system such that it deforms to the adjacent tissue;
    advancing an elongate shaft having forceps toward the deployed prosthetic heart valve;
    grasping a metallic stent of the prosthetic heart valve with the forceps and delivering thermal energy to the ring-shaped body, via the forceps, to heat at least a portion of the ring-shaped body to at least a transition temperature thereby expanding the ring-shaped body; and
    sealing the space between the prosthetic heart valve and the adjacent tissue with the expanded ring-shaped body disposed therebetween.

2. The method of claim 1, wherein the ring-shaped body comprises a solid foam and wherein the step of delivering thermal energy to the ring-shaped body comprises heating the solid foam.

3. The method of claim 1, wherein delivering thermal energy to the ring-shaped body results in uniform radial expansion of the ring-shaped body.

4. The method of claim 1, wherein the ring-shaped body is coupled to the prosthetic heart valve with a friction fit and no additional attachments.

5. The method of claim 1, wherein the ring-shaped body is coupled to the prosthetic heart valve with at least one coupling element selected from the group consisting of sutures, adhesives, staples, and clips.

6. The method of claim 1, wherein:
    prior to loading the prosthetic heart valve into the delivery system, the ring-shaped body is in a deformed state;
    while the prosthetic heart valve is loaded into the delivery system, the ring-shaped body is in a compressed state; and
    upon delivering thermal energy to the ring-shaped body, the ring-shaped body is in a fully expanded state, the ring-shaped body being larger in the deformed state than in the compressed state, and larger in the fully expanded state than in the deformed state.

7. The method of claim 1, wherein the forceps include a pair of jaws coupled to a terminal end of the elongate shaft.

8. The method of claim 7, wherein grasping the prosthetic heart valve with the forceps includes grasping the prosthetic heart valve between the pair of jaws.

9. The method of claim 1, wherein delivering thermal energy to the ring-shaped body includes indirectly delivering thermal energy to the ring-shaped body by delivering thermal energy directly to the metallic stent.

10. The method of claim 1, wherein advancing the elongate shaft toward the deployed prosthetic heart valve includes disposing the forceps at one side of the metallic stent.

11. The method of claim 1, wherein advancing the elongate shaft toward the deployed prosthetic heart valve includes disposing the forceps through an interior of the metallic stent.

* * * * *